United States Patent
Auld et al.

(10) Patent No.: US 12,357,450 B2
(45) Date of Patent: Jul. 15, 2025

(54) HAPTIC OPTIC MANAGEMENT SYSTEM UTILIZING ROTARY ARMS

(71) Applicant: Alcon Inc., Fribourg (CH)

(72) Inventors: Jack Robert Auld, Laguna Niguel, CA (US); Matthew Braden Flowers, Aliso Viejo, CA (US); Matthew Douglas McCawley, San Clemente, CA (US); Andrew Thomas Schieber, Tustin, CA (US); Sudarshan B. Singh, Euless, TX (US); Marcus Antonio Souza, Costa Mesa, CA (US)

(73) Assignee: Alcon Inc, Fribourg (CH)

( * ) Notice: Subject to any disclaimer, the term of this patent is extended or adjusted under 35 U.S.C. 154(b) by 267 days.

(21) Appl. No.: 18/310,982

(22) Filed: May 2, 2023

(65) Prior Publication Data
US 2023/0263621 A1 Aug. 24, 2023

Related U.S. Application Data

(63) Continuation of application No. 16/705,861, filed on Dec. 6, 2019, now Pat. No. 11,678,977.
(Continued)

(51) Int. Cl.
*A61F 2/16* (2006.01)

(52) U.S. Cl.
CPC ...... *A61F 2/167* (2013.01); *A61F 2002/1686* (2013.01); *A61F 2002/1689* (2013.01); *A61F 2002/16905* (2015.04)

(58) Field of Classification Search
CPC ............ A61F 2/167; A61F 2002/16905; A61F 2002/1686; A61F 2002/1689
See application file for complete search history.

(56) References Cited

U.S. PATENT DOCUMENTS

| 11,678,997 B2 * | 6/2023 | Mesiwala | A61B 17/846 |
| | | | 623/17.16 |
| 2007/0270945 A1 * | 11/2007 | Kobayashi | A61F 2/1664 |
| | | | 606/107 |

(Continued)

FOREIGN PATENT DOCUMENTS

| JP | 2011-087976 A | 5/2011 |
| WO | 2004087019 A1 | 10/2004 |
| WO | 2018006889 A2 | 1/2018 |

*Primary Examiner* — Jerrah Edwards
*Assistant Examiner* — Aren Patel
(74) *Attorney, Agent, or Firm* — PATTERSON + SHERIDAN, LLP

(57) ABSTRACT

Systems, methods, and devices for inserting an intraocular lens (IOL) assembly into an eye may be provided. An example optic management system may include a housing having a first end and a second end and a first side extending between the first end and the second end. The housing may include a cavity formed in the first side of the housing and configured to accommodate an intraocular lens, wherein the cavity comprises a first end portion, a second end portion, and a central portion. The housing may further include a bore formed in the housing, wherein a first portion of the bore extends from the first end to the cavity. The haptic optic management system may further include a ceiling disposed on the first side of the housing. The haptic optic management system may further include arms pivotably coupled to the housing in the cavity.

20 Claims, 17 Drawing Sheets

Related U.S. Application Data

(60) Provisional application No. 62/777,919, filed on Dec. 11, 2018.

(56) References Cited

U.S. PATENT DOCUMENTS

| | | | |
|---|---|---|---|
| 2010/0204705 A1 | 8/2010 | Brown et al. | |
| 2011/0144653 A1* | 6/2011 | Pankin | A61F 2/167 |
| | | | 606/107 |
| 2018/0353287 A1* | 12/2018 | Kudo | A61F 2/167 |
| 2018/0368971 A1* | 12/2018 | Zacher | A61F 2/16 |
| 2019/0224002 A1* | 7/2019 | Springer | A61F 2/1667 |
| 2019/0254812 A1 | 8/2019 | Maroschek | |
| 2020/0038171 A1* | 2/2020 | Glick | A61M 5/31505 |

* cited by examiner

HAPTIC OPTIC MANAGEMENT SYSTEM UTILIZING ROTARY ARMS

CROSS-REFERENCE TO RELATED APPLICATIONS

This application is a continuation of U.S. patent application Ser. No. 16/705,861, filed Dec. 6, 2019, which claims benefit of and priority to U.S. Provisional Patent Application No. 62/777,919, filed Dec. 11, 2018, the entire contents of each of which are incorporated by reference in their entirety.

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded natural lens with an intraocular lens ("IOL"). A large incision site may cause a longer post-operation healing time. To reduce this healing time, typical operating procedures have shifted to making incisions of about 2 millimeters in size into the eye. While this smaller size of incision may reduce post-operation healing time, problems such as the size and functionality of the insertion tool may arise as the incision size continues to shrink. Typically, the insertion tool may be pre-loaded with the IOL that may be inserted into the patient's eye once the clouded natural lens is removed. The insertion tool may include a plunger for forcing the IOL out of the nozzle of the insertion tool. The plunger may have additional functions including haptic tucking and folding of the IOL. Once an incision has been made, the insertion tool may be inserted into the eye through the incision, and the folded IOL may be dispensed into the eye by actuation of the plunger. As the incision site decreases, the size of the nozzle of the insertion tool may decrease accordingly.

SUMMARY

In an exemplary aspect, the present disclosure is directed to a haptic optic management system. An example optic management system may include a housing having a first end and a second end and a first side extending between the first end and the second end. The housing may include a cavity formed in the first side of the housing and configured to accommodate an intraocular lens, wherein the cavity comprises a first end portion, a second end portion, and a central portion. The housing may further include a bore formed in the housing, wherein a first portion of the bore extends from the first end to the cavity. The haptic optic management system may further include a ceiling disposed on the first side of the housing. The haptic optic management system may further include arms pivotably coupled to the housing in the cavity.

In another exemplary aspect, the present disclosure is directed to an insertion tool. An example insertion tool may include a drive system. The drive system may include a body. The insertion tool may further include a plunger disposed at least partially in the drive system. The insertion tool may further include a nozzle. The insertion tool may further include a haptic optic management system disposed between the drive system and the nozzle for receiving a distal tip of the plunger. The optic management system may include a housing having a first end and a second end and a first side extending between the first end and the second end. The housing may include a cavity formed in the first side of the housing and configured to accommodate an intraocular lens, wherein the cavity comprises a first end portion, a second end portion, and a central portion. The housing may further include a bore formed in the housing, wherein a first portion of the bore extends from the first end to the cavity. The haptic optic management system may further include a ceiling disposed on the first side of the housing. The haptic optic management system may further include arms pivotably coupled to the housing in the cavity.

In another exemplary aspect, the present disclosure is directed to a method of delivering an intraocular lens. The example method may include rotating a pair of arms such that each of the arms engages a corresponding haptic that extends from an optic of the intraocular lens to move the corresponding haptic up one or more inclined surfaces and onto the optic. The example method may further include applying downward force to the arms with cantilever tabs as each of the arms continues to rotate while in engagement with the corresponding haptic to cause the intraocular lens to fold in upon itself. The example method may further include allowing the arms to spring upwards as the arms rotate past the cantilever labs, wherein the intraocular lens falls into a bore in a housing as the arms spring upwards. The example method may further include actuating a drive system to dispense the intraocular lens from the bore through a nozzle and into an eye, wherein the nozzle is coupled to the housing.

The different aspects may include one or more of the following features. The first portion of the bore may be oval in shape so that the intraocular lens is displaced from the cavity through the first portion with a plunger. The bore may include a second portion that extends from the cavity to the second end and is configured to receiver the plunger. An intraocular lens may be disposed in the cavity, wherein the intraocular lens includes an optic and haptics that extend from the optic. One of the haptics may extend from the optic onto a haptic platform formed in the first end portion. Another one of the haptics may extend from the optic onto a haptic platform formed in the second end portion. A periphery of the optic is disposed on one or more optic platforms formed in the central portion. The central portion may be deeper than the first end portion and the second end portion, wherein a base of the central portion aligns with the first portion of the bore, and wherein the central portion further comprise optic platforms laterally offset from the base and that are raised relative to the base. The first end portion and the second end portion each may comprise a haptic platform for receiving at least a portion of a haptic, an inclined surface positioned between the haptic platform and the central portion, a bore formed in the haptic platform for receiving one of the arms, and an end wall. The arms may each comprise a first end, a second end, a body portion joining the first end and the second end, wherein the arms each further comprise a tab that extends from the first end and a pin that extends from the first end on an opposite side of the arm from the tab, wherein the arm is pivotably about the pin. Each haptic platform may comprise a bore for receiving the pin from the corresponding one of the arms. The ceiling may comprise slots and cantilever tabs disposed in the slots, wherein each of the cantilever tabs is positioned to engage a corresponding one of the arms being rotated in the housing. The cantilever tabs may protrude from a bottom face of the ceiling, and wherein ceiling ramps are formed in the bottom face that slope into the bottom face and form recesses that accommodate haptics of the intraocular lens the haptics are moved in the housing. The plunger of the insertion tool may be operable to engage the intraocular lens in the cavity when the drive system is actuated to dispense the intraocular lens from the nozzle. The drive system may include a lever and a pneumatic system. The arms may be rotated by applying an external force to a tab that extends from each of the arms.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
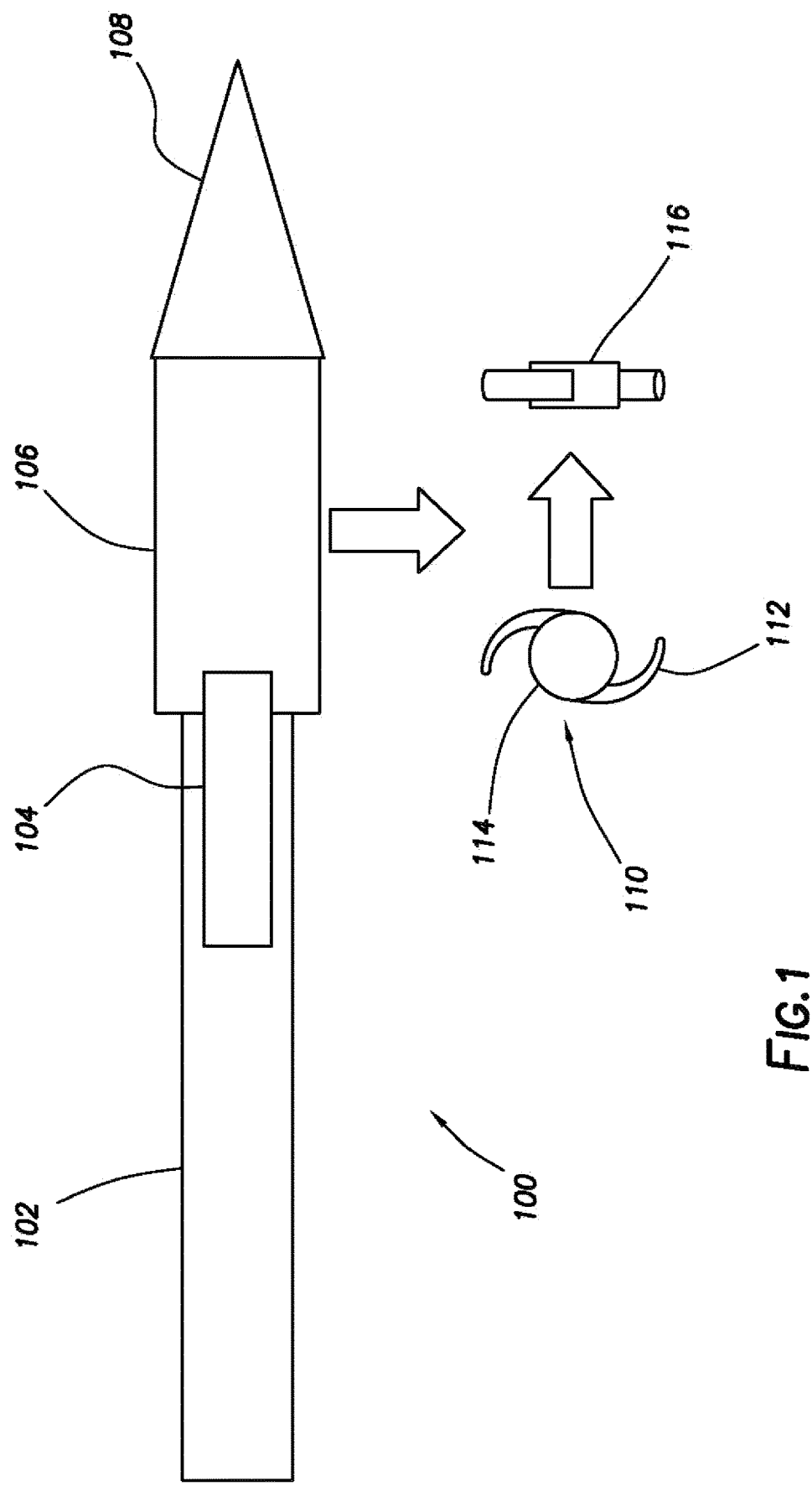
FIG. 1 illustrates a schematic of an example insertion tool operable to deliver an IOL into an eye.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers may be used throughout the drawings to refer to the same or like parts.

The example embodiments described herein generally relate to eye surgery. More particularly, the example embodiments generally relate to systems, methods, and devices for inserting an intraocular lens ("IOL") into an eye. Embodiments may include an insertion tool for preparation and delivery of the IOL into a patient's eye that includes a plunger, a nozzle, and a haptic optic management system. In some embodiments, the haptic management system may fold the IOL and tuck one or more haptics of the IOL. The haptic extends from an optic of the IOL and stabilizes the IOL when disposed within the capsular bag of the eye. After preparation of the IOL, the plunger forces the IOL through the insertion tool and out the nozzle.

FIG. 1 illustrates a schematic of an insertion tool 100. In some embodiments, insertion tool 100 may include a drive system 102, a plunger 104, a haptic optic management system (interchangeably referred to as "HOMS") 106, and a nozzle 108. The drive system 102 may be any system or combination of components operable to actuate the plunger 104. For example, the drive system 102 may utilize a lever and/or pneumatic systems; a manually driven system or component; an electromechanical system; a hydraulic system; or other device operable to drive the plunger 104 to advance; partially advance; or fully deliver an IOL 110 from the insertion tool 100. The plunger 104 is coupled to the drive system 102. The drive system 102 is operable to actuate the plunger 104. For example, the drive system 102 may be powered by, for example, electrically, mechanically, hydraulically, pneumatically, combinations thereof, or in some other manner. In response to the drive system 102, the plunger 104 moves through the HOMS 106. The HOMS 106 may be located between the drive system 102 and the nozzle 108. In alternate embodiments, the HOMS 106 may be disposed at other locations within the insertion tool 100. In some embodiments, the HOMS 106 may contain an IOL 110 in an unfolded position.

The drive system 102 may be any system, component, or group of components operable to advance an IOL 110 through the insertion tool 100. For example, the drive system 102 include plunger, schematically shown as plunger 104 in FIG. 1, that is operable to engage the IOL 110 disposed within the insertion tool 100 and advance the IOL 110 within the insertion tool 100. In some instances, the plunger 104 is operable to expel the IOL from the insertion tool 100.

In some instances, the drive system 102 may be a manually driven system. That is, in some instances, a user applies a force to cause the drive system 102 to operate. An example drive system 102 includes a plunger 104 that is manually engageable directly or indirectly by a user to push the plunger 104 through the insertion tool 100. When advanced, the plunger 104 engages an IOL 110 and advances the IOL 110 through the insertion tool 100, which may also include expelling the IOL 110 from the insertion tool 100. A non-limiting example of a manual IOL insertion tool is shown in U.S. Patent Application Publication No. 2016/0256316, the entire contents of which are incorporated herein by reference in its entirety. According to other implementations, the drive system 102 may be an automated system. Example automated drive systems are shown in U.S. Pat. Nos. 8,808,308; 8,308,736; and 8,480,555, the entire contents of each being incorporated herein by reference in their entirety. Still further, other automated drive systems within the scope of the present disclosure are described in U.S. Pat. No. 8,998,983 and U.S. Patent Application Publication No. 2017/0119522, the entire contents of each being incorporated herein by reference in its entirety. While example drive systems are provided as examples, these systems are not intended to be limiting. Rather, any component, group of components, systems, devices, mechanisms, or combinations thereof operable to advance an IOL 110 is within the scope of the present disclosure.

As shown in FIG. 1, the IOL 110 is a single piece IOL that includes an optic 114 and haptics 112 extending from opposing sides of the optic 114. For example, in the example IOL 110 shown in FIG. 1, the haptics 112 are disposed 180° relative to each other along an outer periphery of the optic 114. However, other types of IOLs are within the scope of the disclosure. For example, a multi-piece IOL, in which the optic and one or more haptics are separate components, may also be used.

Figure 2A:
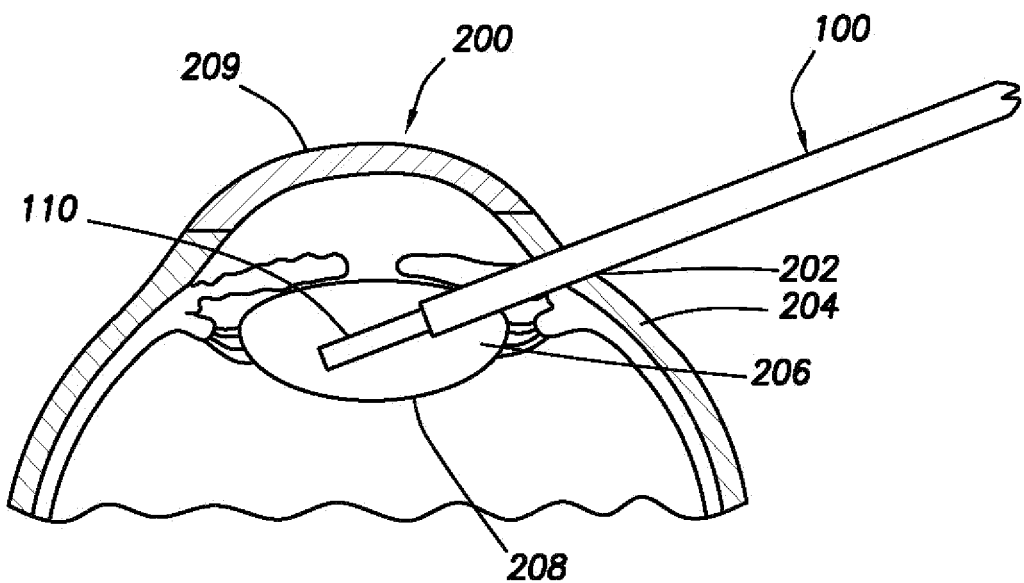
FIG. 2A illustrates an eye in which an IOL is being introduced from an insertion tool.

The IOL 110 may have a shape similar to that of a natural lens of an eye (e.g., eye 200 shown in FIG. 2A). The IOL 110 may be made from a numerous materials including, but not limited to, silicone, acrylic, and/or combinations thereof. Other materials are also contemplated. The haptics 112 extend from a periphery of the optic 114 and function to stabilize the IOL 110 when disposed within an eye.

In some instances, the HOMS 106 may be actuated to tuck the haptics 112 over the optic 114 and fold the optic 114. For example, the HOMS 106 may operate to fold the haptics 112 over the optic 114 and fold the optic 114 over or around the folded haptics 112. The IOL 110 is shown in a folded configuration at 116. The folded configuration 116 of the optic 114 may involve one or more haptics 112 folded relative to the optic 114 and, in some instances, the optic 114 folded relative to one or more of the haptics 112. The plunger 104 may be advanced through the HOMS 106 once the HOMS 106 has folded the IOL 110. As the plunger 104 moves through the HOMS 106, the plunger 104 displaces the folded IOL 110 from the HOMS 106. For example, the plunger 104 may force the folded IOL 110 into and through the nozzle 108.

FIG. 2A illustrates an eye 200 of a patient undergoing an operation with insertion tool 100. As illustrated, the insertion tool 100 dispenses a folded IOL 110 into the eye 200 of a patient. In some embodiments, an incision 202 is made in the eye 200 by a surgeon, for example. For example, in some instances, the incision 202 may be made through the sclera 204 of the eye 200. In other instances, an incision may be formed in the cornea 209 of the eye 200. The incision 202 may be sized to permit insertion of a portion of the insertion tool 100 in order to deliver the folded IOL 110 into the capsular bag 208. For example, in some instances, the size of the incision 202 may have a length less than about 2000 microns (2 millimeters). In other instances, the incision 202 may have a length of from about 0 microns to about 500 microns, from about 500 microns to about 1000 microns, from about 1000 microns to about 1500 microns, or from about 1500 microns to about 2000 microns.

After the incision 202 is made, the insertion tool 100 is inserted through the incision into an interior portion 206 of the eye 200. The insertion tool 100 is actuated to dispense the folded IOL 110 into the capsular bag 208 of the eye 200. Upon dispensation, the folded IOL 110 reverts to an initial, unfolded state, and the IOL 110 settles within the capsular bag 208 of the eye 200, as shown on FIG. 2B. The capsular bag 208 holds the IOL 110 within the eye 200 in a relationship relative to the eye 200 so that the optic 114 refracts light directed to the retina (not shown). The haptics 112 of the IOL 110 engage the capsular bag 208 to secure the IOL 110 therein. After dispensing the IOL 110 into the capsular bag 208, the insertion tool 100 is removed from the eye 200 through the incision 202, and the eye 200 is allowed to heal over a period of time.

Figure 2B:
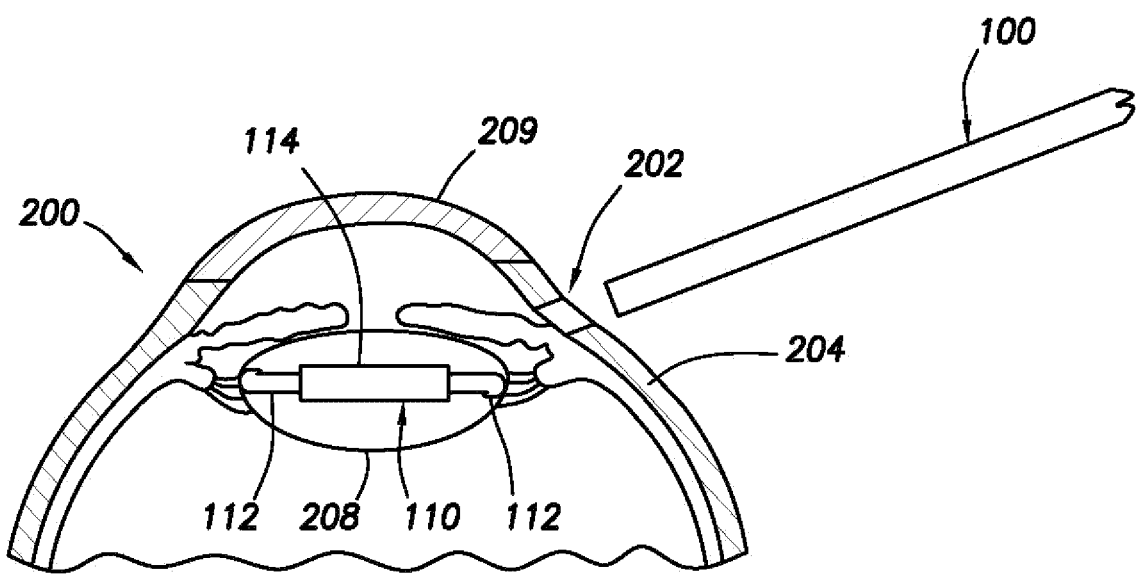
FIG. 2B illustrates the eye shown in FIG. 2A in which the IOL is positioned within the capsular bag of the eye and the insertion tool removed from the eye.
Figure 3:
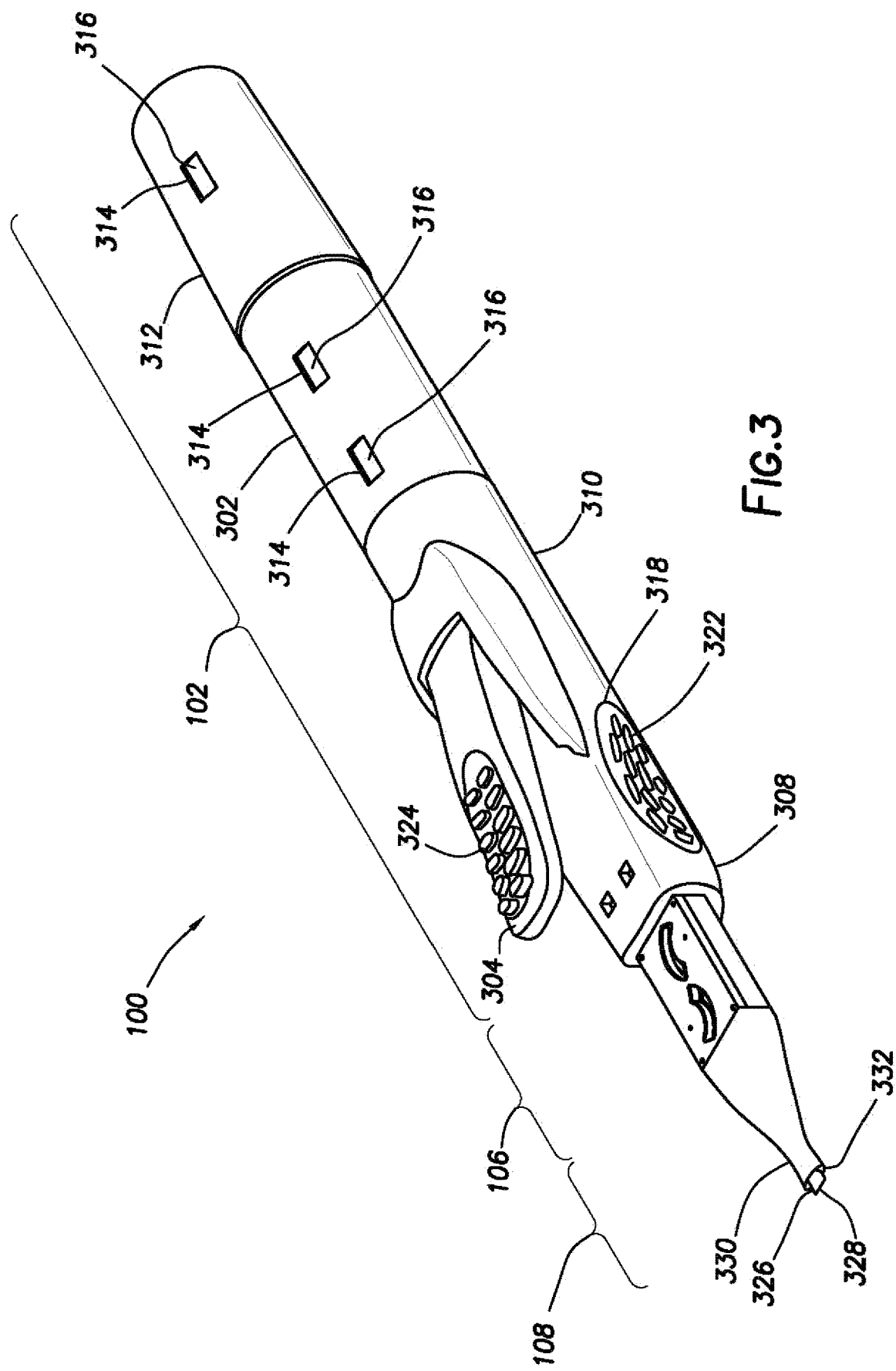
FIG. 3 illustrates a perspective view of another example insertion tool operable to delivery an IOL into an eye.
Figure 4:
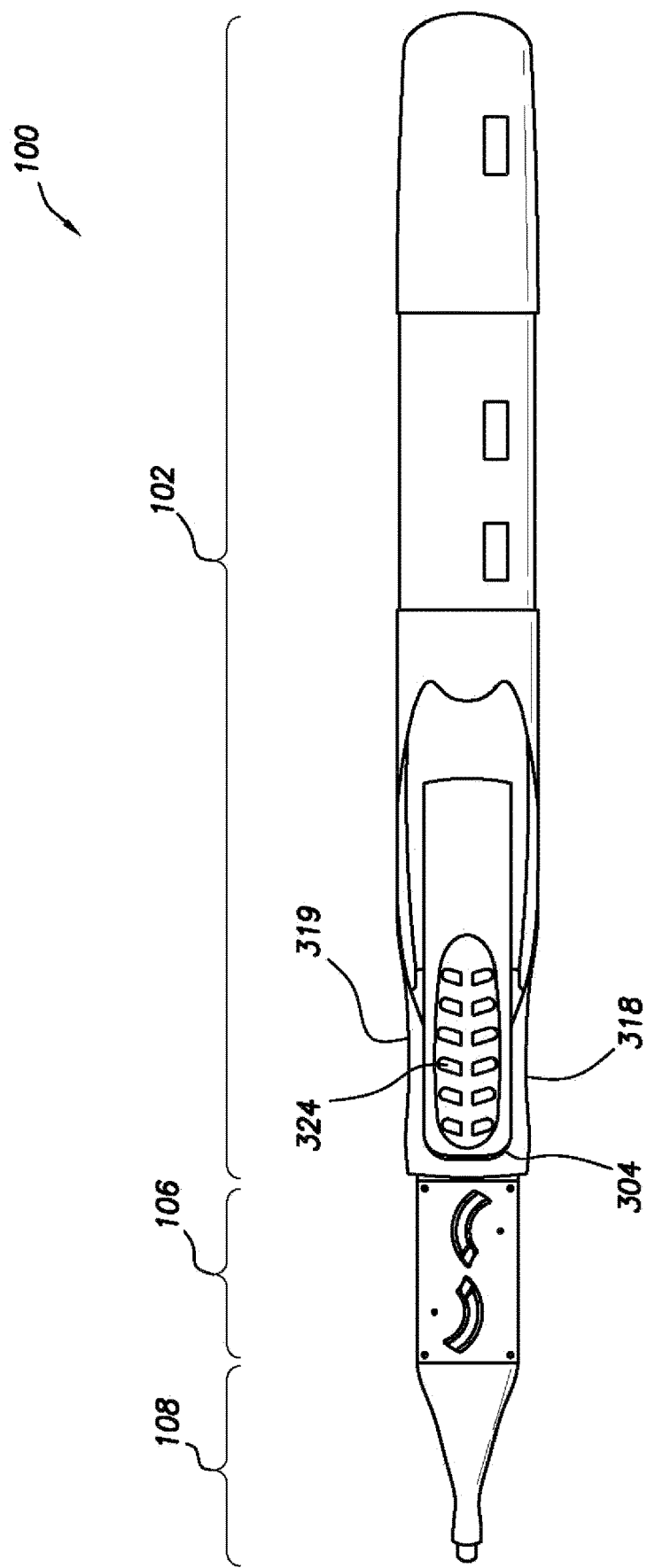
FIG. 4 illustrates a top view of the insertion tool of FIG. 3.
Figure 5:
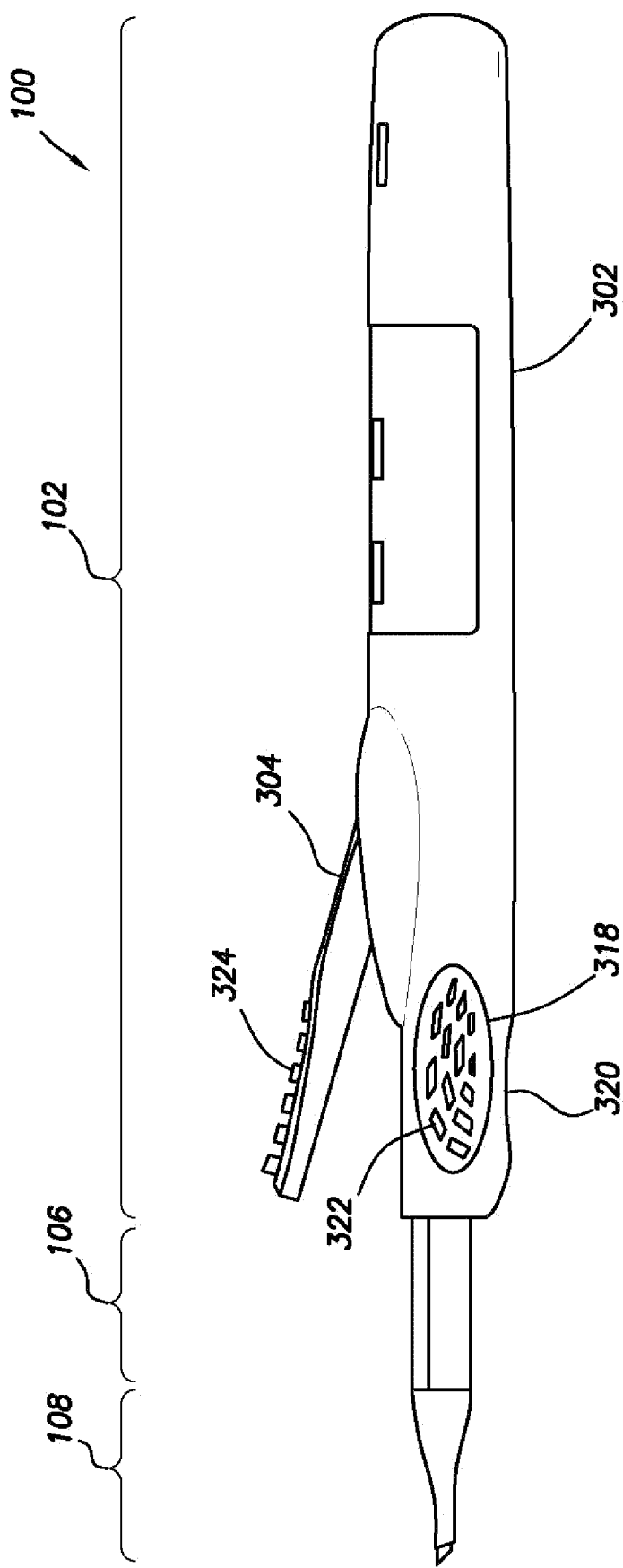
FIG. 5 illustrates a side view of the insertion tool of FIG. 3.

FIGS. 3-5 illustrate an example insertion tool 100 operable to deliver an IOL into the eye (e.g., IOL 110 in eye 200 shown on FIGS. 2A and 2B). As illustrated, the insertion tool 100 includes a drive system 102, a haptic optic management system 106, and a nozzle 108. The insertion tool 100 may also include a plunger, which may be similar to the plunger 104 shown in FIG. 1. In some instances, The plunger 104 may be actuated to advance an IOL, e.g., which may be similar to the IOL 110 shown in FIG. 1, within the insertion tool 100 and, in some cases, dispense the IOL 110 from the insertion tool 100.

Referring to FIG. 3, the drive system 102 includes a body 302 and a lever 304 that may be pivotally coupled to the body 302. The nozzle 108 is coupled to a distal end 308 of the body 302. The HOMS 106 is disposed between the body 302 and the nozzle 108. In some instances, the nozzle 108 may be integrally connected to the body 302. In other instances, the nozzle 108 may be separate from the body 302 and may be coupled to the body 302 via an interlocking relationship. In some instances, the HOMS 106 and the nozzle 108 may be integrally formed. In other instances, the HOMS 106, the nozzle 108, and the body 302 may be integrally formed.

In some instances, the body 302 may have a slender, elongated shape. In some instances, the body 302 may have a first portion 310 and a second portion 312. In some instances, the second portion 312 may be at least partially disposed over the first portion 310. In the example shown, the second portion 312 includes a plurality of apertures 314. A plurality of tabs 316 formed on the first portion 310 are received into the apertures 314 to join the first portion 310 and the second portion 312. The tabs 316 may form an interlocking fit with the apertures 314. However, the construction of the body 302 of the example insertion tool 100 shown in FIGS. 3-5 is merely a non-limiting example. In some instances, the body 302 may be a single unitary piece. In some instances, the body 302 may include one or more cylindrical pieces. Moreover, the body 302 may be constructed in any desirable manner from any number of components.

With reference to FIGS. 3-5, the body 302 also includes reliefs 318, 319, and 320. The reliefs 318, 319, and 320 are shallow recesses formed in the body 302 to accommodate, for example, one or more fingers of a user. One or more of the reliefs 318, 319, and 320 may include a textured surface 322 that may provide a user with an improved grip of and control over the insertion tool 100. As shown in FIGS. 3 and 5, the relief 318 may include texture surface 322. However, the scope may not be so limited. Rather any, all, or none of the reliefs 318, 319, and 320 may include the textured surface 322. Similarly, the lever 304 may also include a textured surface 324. However, in some instances, the lever 304 may not include a textured surface.

Referring to FIG. 3, the nozzle 108 includes a distal tip 326 that defines an opening 328. The nozzle 108 also includes a flared portion or wound guard 330. The distal tip 326 may be adapted to be inserted into an incision formed in an eye, such as the incision 202 in eye 200 shown on FIGS. 2A and 2B, in order to deliver a folded IOL there into. The wound guard 330 may include an end surface 332 operable to contact an exterior surface in order to limit a depth to which the distal tip 326 penetrates the eye 200. In some embodiments, the wound guard 330 may be omitted.

In some embodiments, the insertion tool 100 may be preloaded. That is, the insertion tool 100 may include an IOL disposed therein when provided to an end user. In some instances, the IOL may be disposed within the insertion tool 100 in an unfolded state and ready to be delivered into a patient. Having the insertion tool 100 preloaded with an IOL reduces the number of steps a user must perform both before delivering the IOL into a patient. For example, a preloaded insertion tool obviates any steps a user would otherwise be required to perform in order to load the insertion tool with the IOL. With a reduced number of steps, error and risk associated with delivery of the IOL into a patient may be reduced. Further, an amount of time required to deliver the IOL may also be reduced. In some embodiments, the IOL may be pre-loaded into the haptic optic management system 106.

Figure 6:
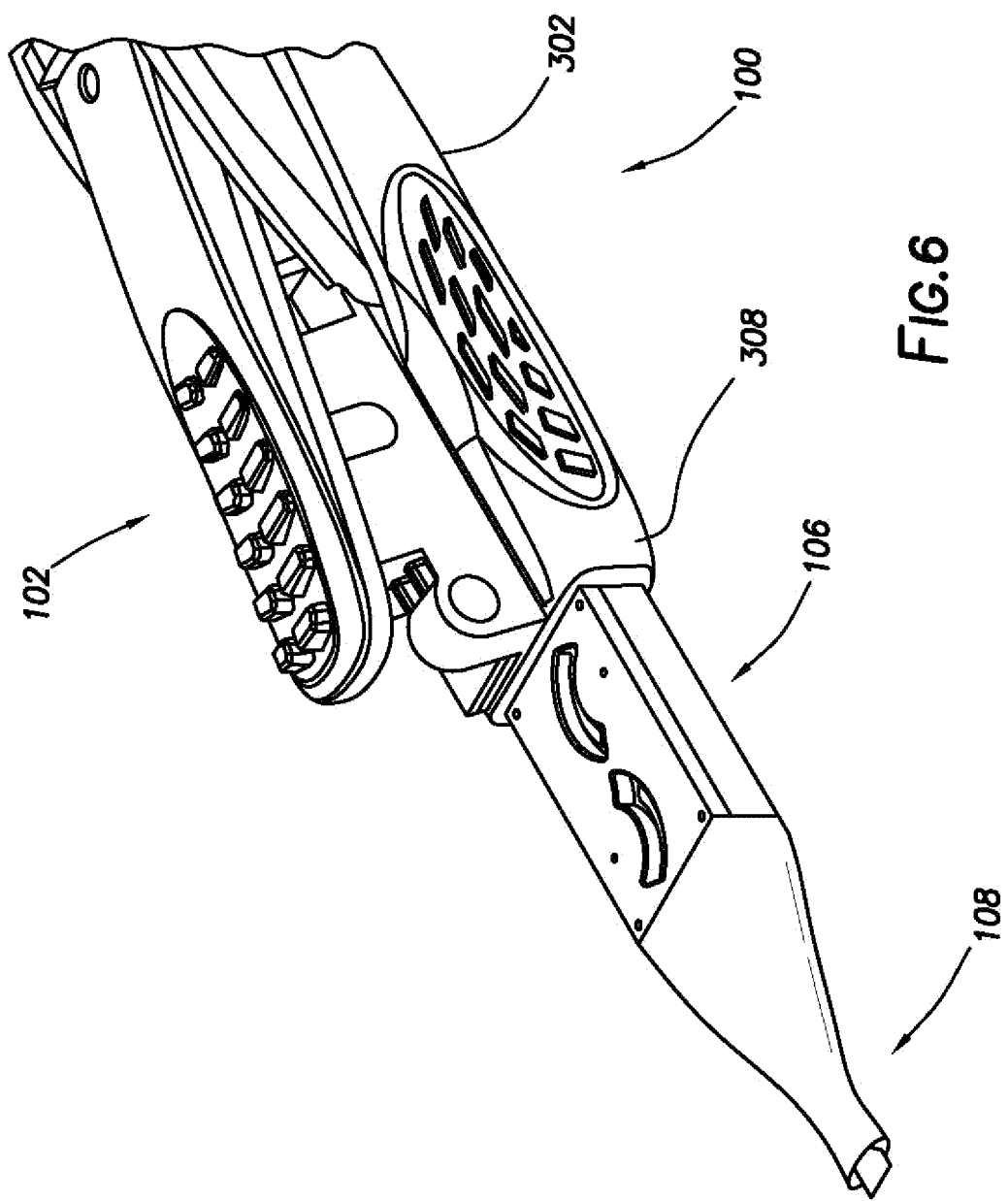
FIG. 6 is a detail view of a distal end of the insertion tool of FIG. 3.

FIG. 6 illustrates a close-up view of an example insertion tool 100 with a haptic optic management system 106. The HOMS 106 is operable to folds the IOL. For example, in some instances, the HOMS 106 may be operable to fold an IOL from an unstressed condition to a fully folded configuration, as shown in FIG. 1, for example. During folding, the HOMS 106 may tuck or fold the haptics 112 over the optic 114 of the IOL 110 as well as fold edges of the optic 114 over the tucked haptics 112, capturing the haptics 112 and thereby placing the IOL 110 into the folded configuration, as shown in FIG. 1, for example.

As shown in FIGS. 3-6, for example, the HOMS 106 is sized to commensurate with a size of the insertion tool 100. That is, the HOMS 106 has a compact size to avoid or limit an amount of obstruction to a surgeon's view while inserting an IOL into an eye. However, the scope of the disclosure is not so limited. Rather, in some instances, a size and/or shape of the haptic optic management system may be selected to be any desired size or shape. Further, while the HOMS 106 is shown disposed at the distal end of the insertion tool 100, the haptic optic management system 106 may be disposed anywhere within or along the insertion tool 100. In some embodiments, the HOMS 106 may be disposed between the nozzle 108 and the drive system 102.

In the illustrated example of FIGS. 3-6, the HOMS 106 is disposed between the distal end 308 of the body 302 and the nozzle 108. In some instances, the HOMS 106 may be removably coupled to the nozzle 108 and/or the drive system 102. For example, the HOMS 106 may be removable coupled to the body 302 with the use of fasteners or adhesives. In still other implementations, the HOMS 106 may couple to the body 302 by a snap-fit engagement or any other desired method of connection. Without limitation, example fasteners may include nuts and bolts, washers, screws, pins, sockets, rods and studs, hinges and/or any combination thereof.

Figure 7:
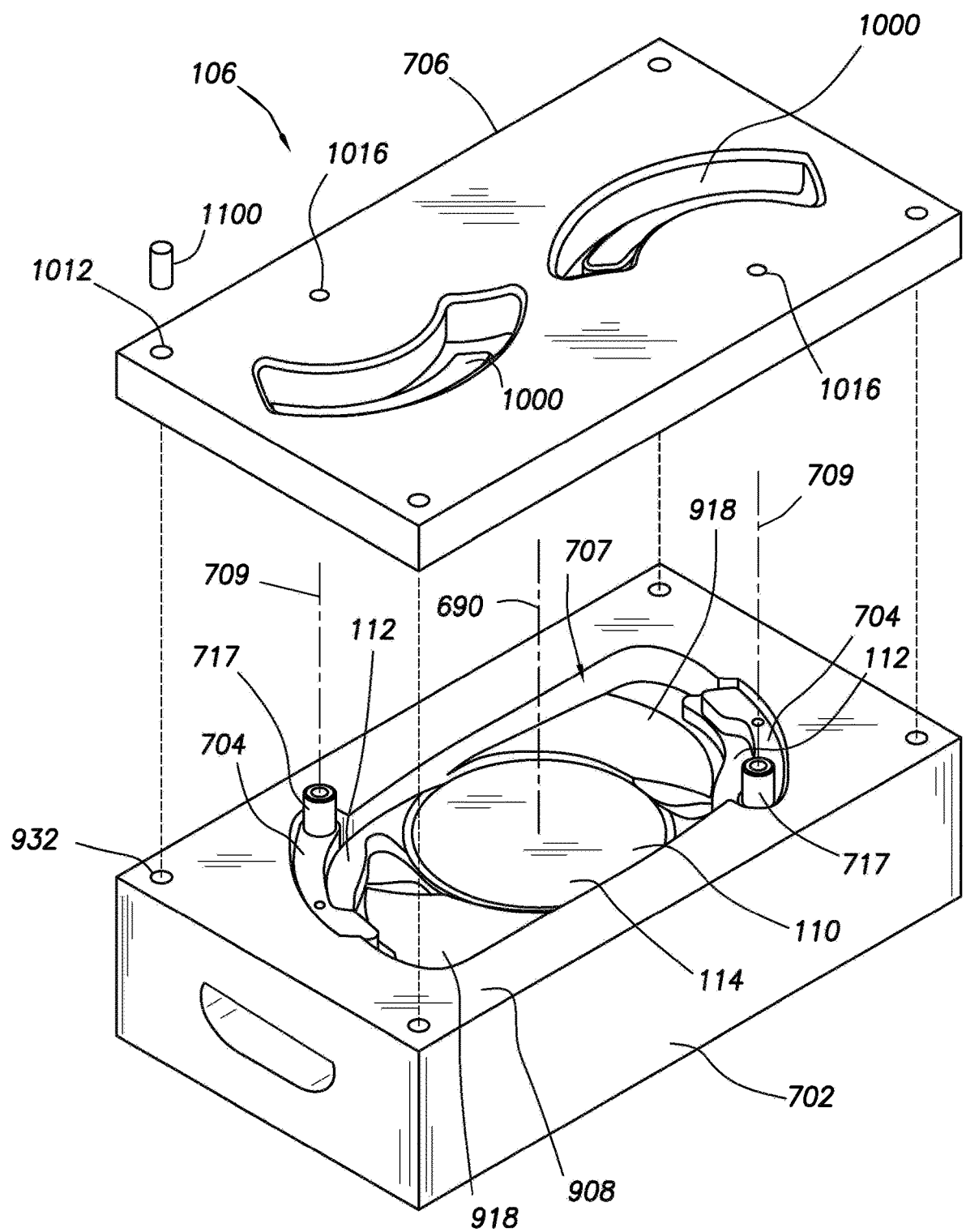
FIG. 7 illustrates an example haptic optic management system.

FIG. 7 illustrates an example haptic optic management system 106. In the illustrated example, the HOMS 106 includes a housing 702 and arms 704 coupled to the housing 702. As illustrated, the HOMS 106 further includes a ceiling 706 disposable on the housing 702. The housing 702 forms a cavity 707 that receives the IOL 110. As illustrated, the IOL 110 is disposed in the cavity 707 formed in the housing 702.

The arms 704 are pivotably attached to the housing 702 and pivot about respective axes 709. In some instances, the axes 709 may be parallel to an optical axis 690 of the optic 114. In other implementations, the axes 709 may have other orientations relative to the optic 114. Each of the arms 704 engages one of the haptics 112. When actuated, the arms 704 cause the haptics 112 to fold over and onto the optic 114. Continued movement of the arms 704 further roll the IOL 110 into a U-shape, such as the folded configuration shown in FIG. 1. Each of the arms includes a tabs 717 extending therefrom. The tabs 717 may be utilized to rotate the arms 704 about the axes 709. In some instances, a user may engage the tabs 717 to actuate the arms 704. In other instances, a device, mechanism, or system may be utilized to actuate the arms 704.

In some cases, the IOL involves a base comprising a ring and haptics extending from the ring. In these cases, an IOL base can be inserted into an eye in a first surgical step and a separate optic can be inserted and coupled with the base at a second surgical step. Furthermore, the optic can be decoupled from the base and a further optic can be inserted and coupled to the already installed base at a subsequent surgical step.

Figure 8:
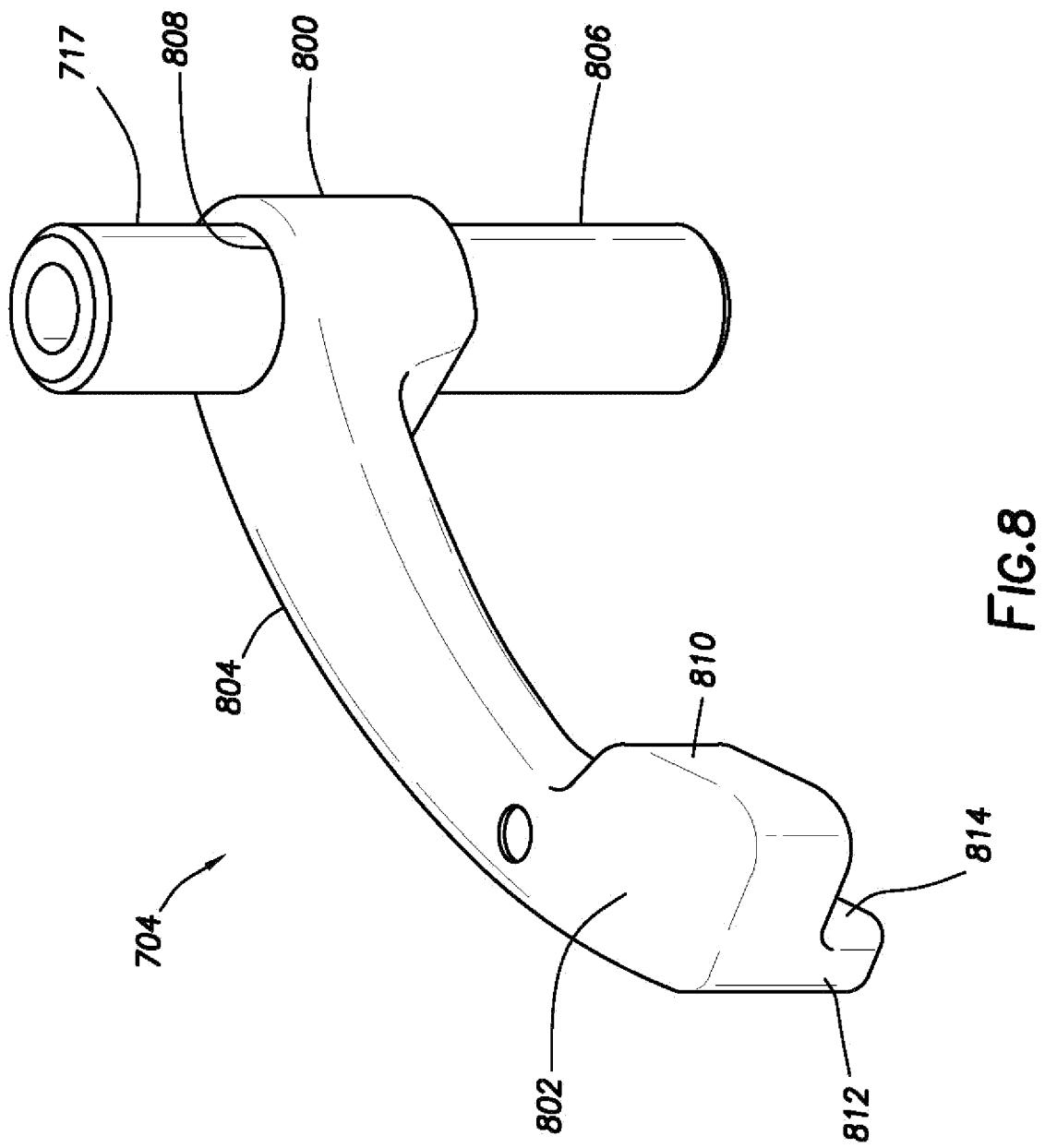
FIG. 8 illustrates an arm of the haptic optic management system of FIG. 7.

FIG. 8 is a perspective view of the arm 704. The arm 704 includes a first end 800 and a second end 802. A body portion 804 joins the first end 800 and the second end 802. In some embodiments, the body portion 804 is generally arcuate in shape. However, other suitable shapes may also suitable for the body portion 804, including a generally angular shaped formed by straight portions joined at a bend, for example. A pin 806 extends from the first end 800. The pin 806 is received in a bore formed in the housing 702 (discussed in more detail below), and the arm 704 pivots about the pin 806. The tab 717 extends from the first end 800 on a side of the arm opposite the pin 806. In some embodiment, the tab 717 is formed by the pin 806 extending through pin bore 808 in the first end 800. As explained above, the tab 717 may be used to actuate the arm 704 so as to pivot the arm 704 about the pin 806. While the tab 717 and the pin 806 are both shown at the first end 800, it is contemplated that the tab 717 and the pin 806 may be disposed at opposite ends of the arm. While not illustrated, the tab 717 may be disposed at the second end 802 and may be used to actuate the arm 704 to pivot about the pin 806 at the first end 800. The arm 704 also includes a protrusion 810 extending from the second end 802. The arm 704 also includes a ledge 812 that projects from the second end 802 on a side of the arm 704 opposite the tab 717. As illustrated, the ledge 812 projects downward beneath protrusion 810. The ledge 812 includes a haptic contact face 814. The haptic contact face 814 is operable to engage a haptic of an IOL to fold the haptic during actuation of the HOMS (e.g., HOMS 106 shown on FIG. 7).

Figure 9:
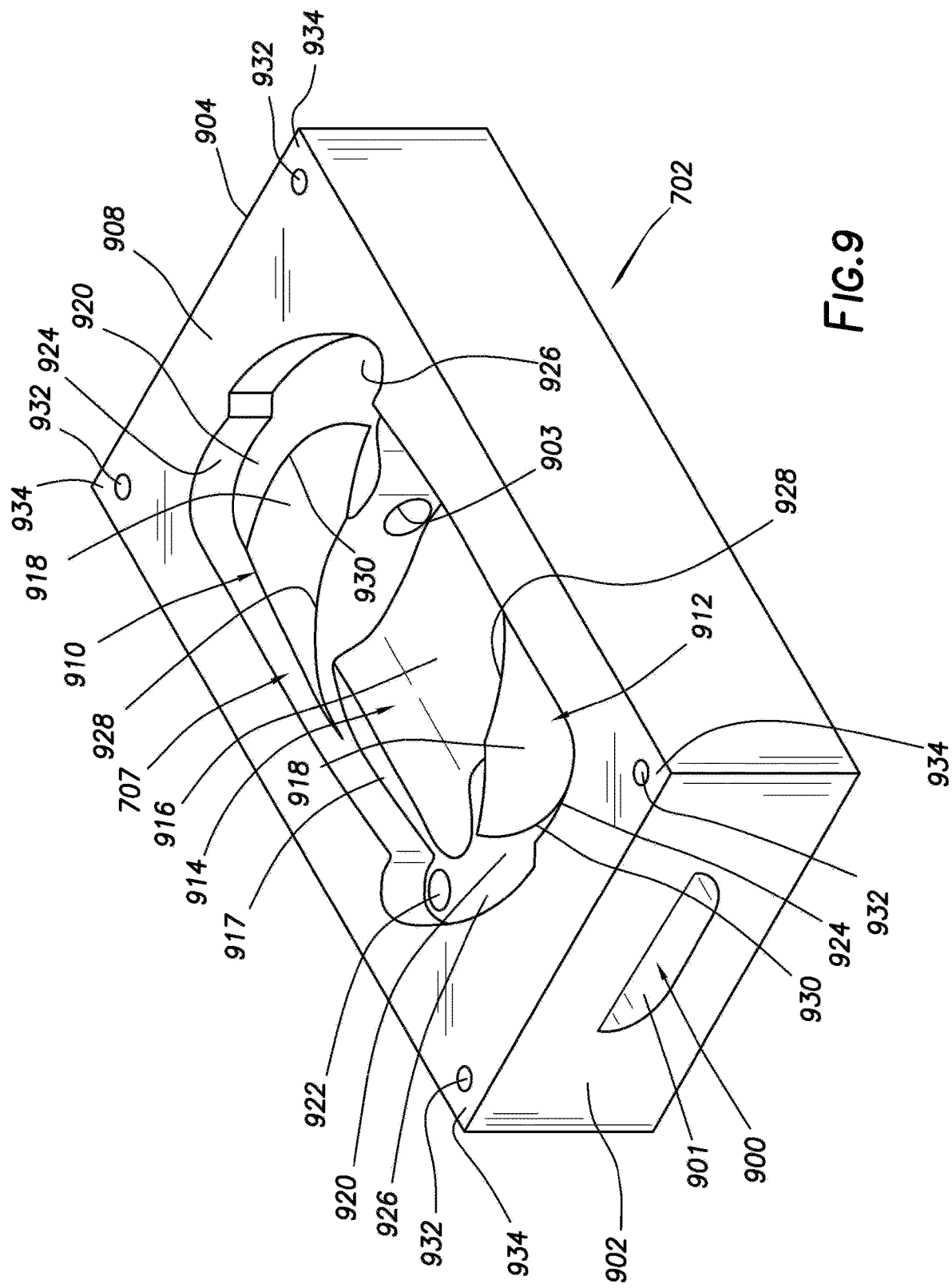
FIG. 9 illustrates a housing of the haptic optic management system of FIG. 7.

FIG. 9 shows the housing 702. The housing 702 may be made from materials, such as, for example, metals, nonmetals, polymers, ceramics, and/or combinations thereof. The housing 702 may have any size and/or shape. For example and without limitation, the housing 702 may be shaped such that all or a portion of the housing 702 may have a cross-sectional shape that is circular, elliptical, triangular, rectangular, square, hexagonal, and/or combinations thereof. In other embodiments, all or a portion of the housing 702 may have a rectangular cross-sectional shape.

The housing 702 includes a bore 900 that traverses an entire length of the housing 702 from a first end 902 of the housing 702 to a second end 904 of the housing 702. The bore 900 defines a path through which a plunger advances to engage an IOL and drive the IOL through the HOMS, such as HOMS 106 shown on FIG. 1). In some implementations, as shown on FIG. 1, the plunger 104 continues to drive the IOL 110 through the nozzle 108 of the insertion tool 100 and expel the IOL 110 from the insertion tool 100. In the example shown in FIG. 9, a first portion 901 of the bore 900 extending distally from the cavity 707 formed in the housing 702 has a U-shaped cross-section. However, the scope of the disclosure is not so limited. In other implementations, the first portion 901 may have a cross-sectional shape that is circular, oval, rectangular, square, triangular, polygonal, or any other cross-sectional shape. A second portion 903 of the bore 900 has a smaller cross-sectional size than that of the first portion 901. Further, the cross-sectional shape of the second portion 903 is different than that of the first portion 901. Particularly, as shown in FIG. 9, the second portion 903 has a circular cross-sectional shape. However, other cross-sectional shapes and sizes of the first portion 901 and second portion 903, such as those described above for the first portion 901, are within the scope of the present disclosure. Further, in some instances, the cross-sectional sizes and shapes of the first portion 901 and the second portion 903 may be the same. The cross-sectional size of the second portion 903 may be smaller from that of the first portion 901 because the second portion 903 may be used to pass the plunger, which generally has a smaller size than a folded IOL, such as folded configuration 116 for the IOL 110 shown on FIG. 1.

The cavity 707 is formed in a first surface 908 of the housing 702 and receives an IOL there into (e.g., IOL 110 shown on FIG. 7). The cavity 707 includes a first end portion 910, a second end portion 912, and a central portion 914. The central portion 914 is deeper than the first end portion 910 and the second end portion 912 in that the central portion 914 extends a greater distance into the housing 702. An IOL is received into the cavity 707 of the housing 702 such that the optic of the IOL is suspended over the central portion 914. A base 916 of the central portion 914 may conform to that of the first portion 901 of the bore 900. Thus, in the illustrated example, the base 916 has a cross-sectional shape that is U-shaped. The central portion 914 also includes optic platforms 917 laterally offset from the base 916. One of the optic platforms 917 is obstructed in FIG. 9 by a portion of the housing 702. The optic platforms 917 are raised relative to the base 916 but are recessed below the first end portion 910 and the second end portion 912. The optic platforms 917 may engage a periphery of the optic 114 (e.g., shown on FIG. 7) to support the IOL 110 in the cavity 707.

Each of the first end portion 910 and the second end portion 912 include an inclined surface 918, a haptic platform 920, a bore 922 formed in the haptic platform 920, and an end wall 924. One of the bores 922 is obstructed by a portion of the housing 702. The end walls 924 have an arcuate shape that conforms to curvature of the haptics 112 of an IOL (e.g., IOL 110 shown on FIG. 7). The curvature of the end wall 924 assists in keeping the IOL retained within the housing 702 in a desired orientation. In other implementations, the end walls 924 may have other shapes. For example, the shape of the ends walls 924 may be a non-arcuate shape that conforms to a non-arcuate shaped haptic. In still other implementations, the end walls 924 may have a shape that does not correspond or otherwise conform to a shape of the haptics of an IOL. The end walls 924, in combination with the haptic platforms 920 form recesses 926. The recesses 926 are adapted to receive the arms 704 when the arms 704 are in an unactuated condition.

The haptic platforms 920 of the first end portion 910 and the second end portion 912, disposed between the ends walls 924 and the inclined surfaces 918, define surfaces that receive the haptics 112 of an IOL 110 (e.g., shown on FIG. 7) when the IOL 110 is in an unstressed condition. The haptic platforms 920 assist in positioning the IOL 110 disposed within the cavity 707 of the housing 702 in a desired orientation. The arms 704 (e.g., shown on FIGS. 7 and 8) are supported by the haptic platforms 920 in the recesses 926 formed in the end walls 924, with the pins 806 (e.g., shown on FIG. 8) of the arms 704 received into the bores 922. As mentioned above, the arms 704 are pivotable about the pins 806 within the bores 922. The inclined surfaces 918 operate to lift the haptics 112 of an IOL 110 over the optic 114 as the haptics 112 are displaced by the arms 704. The inclined surfaces 918 may be positioned between the central portion 914 of the cavity 707 and the haptic platforms 920. A first end 928 of inclined surfaces 918 may tangentially align with the central portion 914 of the cavity 707. A second end 930 of the inclined surfaces 918 may be adjacent to the haptic platforms 920.

With continued reference to FIG. 9, the cavity 707 is shown disposed in first surface 908 of the housing 702. The first surface 908 may also include one or more holes 932 formed therein. In some embodiments, the one or more holes 932 are formed in each corner 934 of the first surface 908. For example, the first surface 908 includes four of the holes 932 with one of the holes 932 formed in each corner 934. However, it is also contemplated the first surface 908 may include more or less than four of the holes 932.

Figure 10A:
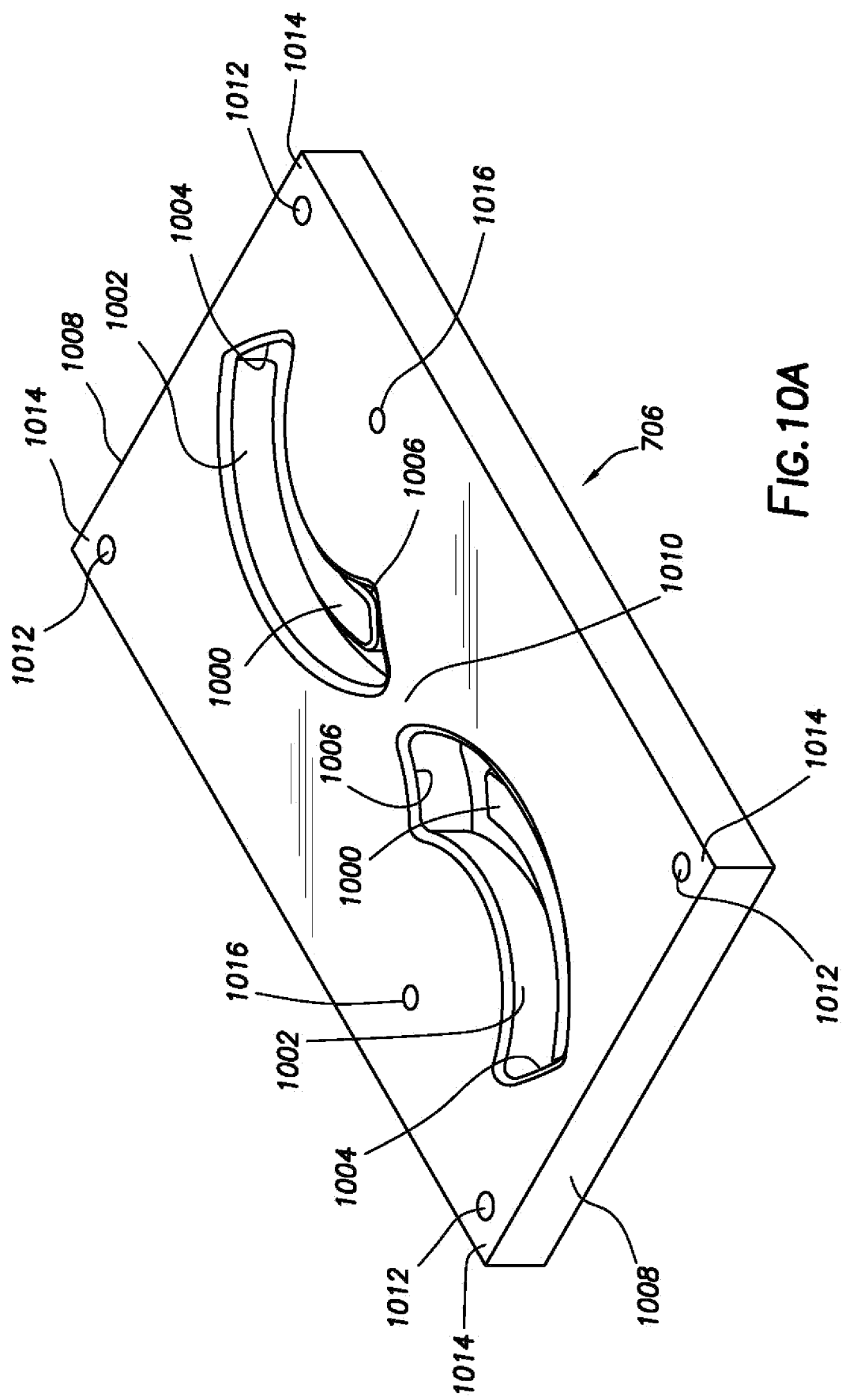
FIG. 10A illustrates a top perspective view of a ceiling of the haptic optic management system of FIG. 7.

FIG. 10A is a top perspective view of the ceiling 706. The ceiling 706 protects the internal components of the HOMS 106 (e.g., referring to FIG. 7) from external elements. In some embodiments, the ceiling 706 includes cantilever tabs 1000. The cantilever tabs 1000 may be set at any suitable angle so as to engage the arms 704 (e.g., referring to FIG. 7) as they are actuated in the housing 702. Each of the cantilever 1000 may be disposed in any suitable fashion within the ceiling 706. The cantilever tabs 1000 may be positioned in the ceiling 706 so that each of the cantilever tabs 1000 is positioned over a corresponding one of the inclined surfaces 918 when the HOMS 106 is assembled. As illustrated, the ceiling 706 also includes slots 1002. In the illustrated example, the cantilever tabs 1000 are each disposed in a corresponding one of the slots 1002. As illustrated, the slots 1002 and corresponding cantilever tabs 1000 may be arcuate in shape, but the slots 1002 and cantilever tabs 1000 may also be otherwise formed, as desired for a particular application. For example, the slots 1002 and cantilever tabs 1000 may be straight or bent in form. The slots 1002 each include a first end 1004 and a second end 1006. The first ends 1004 of the slots 1002 extend from at or near opposing ends 1008 of the ceiling 706 towards a central portion 1010 of the ceiling 706. In the present instance, the cantilever tabs 1000 are attached to the first ends 1004 of the slots 1002 and extend toward the second end 1006, but are not be coupled to the second end 1006.

In examples, the ceiling 706 includes one or more post holes 1012. The post holes 1012 may be disposed at any suitable location. In some embodiments, the one or more post holes 1012 are formed in each corner 1014 of the ceiling 706. For example, the ceiling 706 includes four of the post holes 1012 with one of the post holes 1012 formed in each corner 1014. However, it is also contemplated the ceiling 706 may include more or less than four of the holes 1012. In some embodiments, the ceiling 706 may also include a number of additional holes, shown on FIG. 10A as arm holes 1016.

Figure 10B:
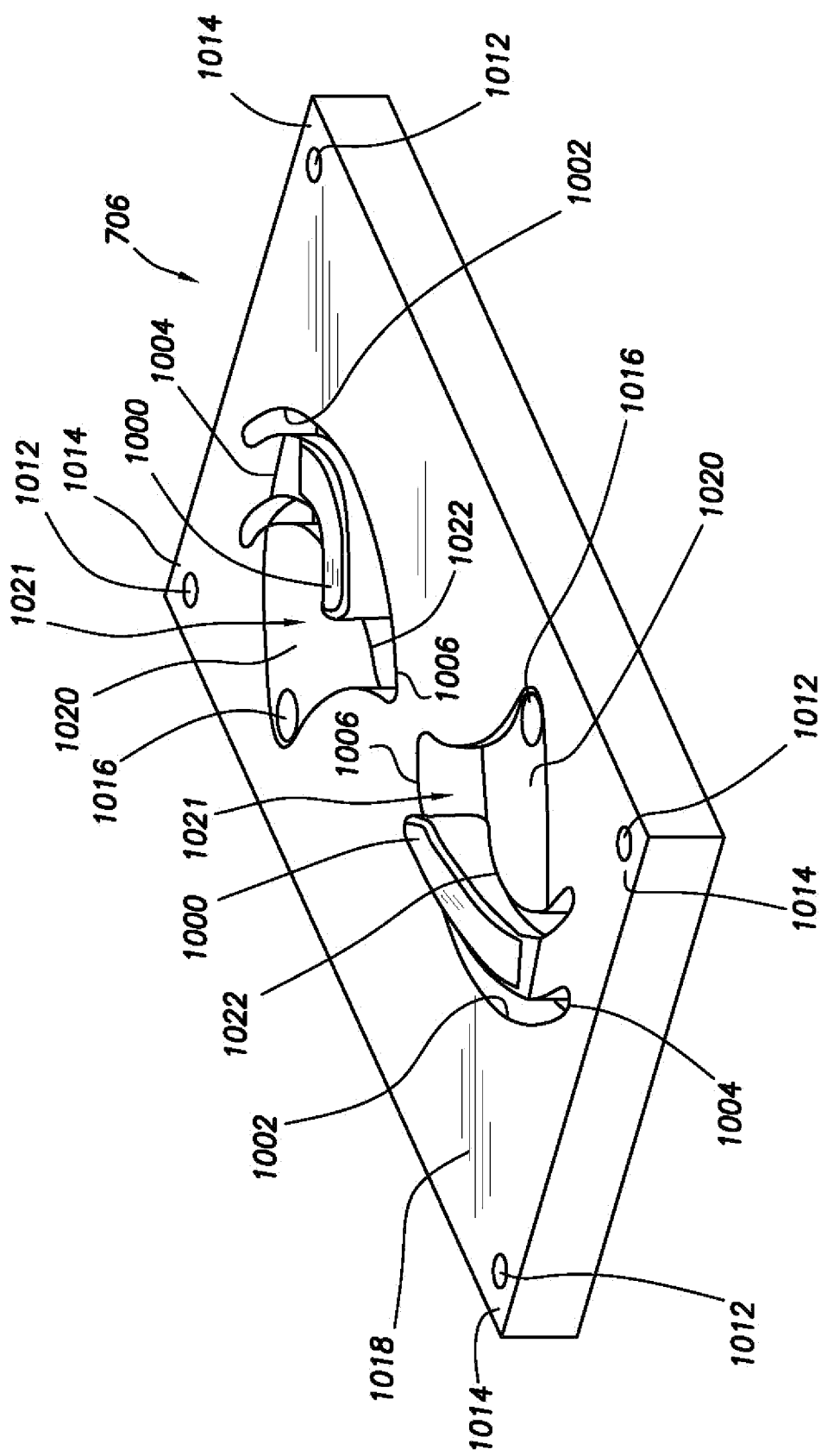
FIG. 10B illustrates a bottom perspective view of a ceiling of the haptic optic management system of FIG. 7.

FIG. 10B is a bottom perspective view of the ceiling 706. As illustrated, the ceiling 706 includes a bottom face 1018. The bottom face 1018 is exposed to the inner components of the HOMS 106 (e.g., referring to FIG. 7) when the HOMS 106 is assembled. The post holes 1012 at the corners 1014 of the ceiling 706 penetrate through the bottom face 1018. The arm holes 1016 also penetrate through the bottom face 1018. In the illustrated example, the cantilever tabs 1000 are disposed in the slots 1002 in the ceiling 706. The cantilever tabs 1000 are attached at the first end 1004 of the slots 1002 and extend toward the second end 1006 of the slots 1002. The cantilever tabs 1000 are not attached at the second end 1006. The cantilever tabs 1000 protrude from the bottom face 1018 of the ceiling 706 such that the cantilever tabs 1000 are ramped from the first end 1004 to the second end 1006. As the cantilever tabs 1000 are not attached at the second end 1006, a force may be applied to the cantilever tabs 1000, opposite the first end 1004, to cause the cantilever tabs 1000 to deflect into the slots 1002 at the second end 1006. The ceiling 706 may also include ceiling ramps 1020 formed in the bottom face 1018. In the illustrated embodiment, the ceiling ramps 1020 slope into the ceiling 706, forming recesses 1021 in the bottom face 1018 that accommodate the haptics 112 (e.g., shown on FIG. 7) as they are moved through the housing 702. Each of the ceiling ramps 1020 may correspond with one of the slots 1002. As illustrated, the ceiling ramps 1020 each form an edge 1022 of a corresponding one of the slots 1002.

Figure 11:
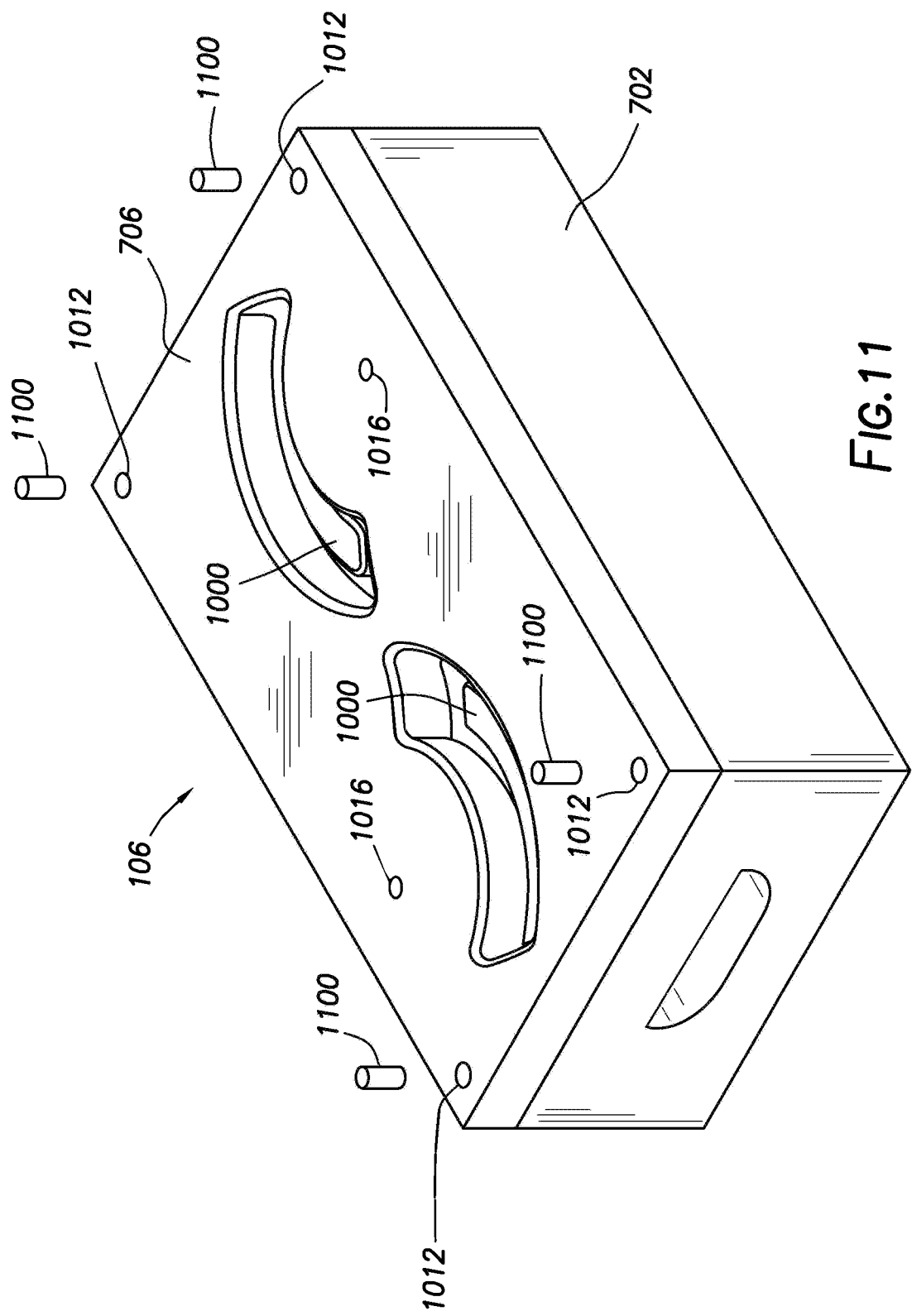
FIG. 11 illustrates a housing with a ceiling of the haptic optic management system of FIG. 7.

FIG. 11 illustrates a perspective view of the HOMS 106 with the ceiling 706 disposed on top of the housing 702. Any suitable technique may be used to secure the ceiling 706 to the housing 702. In examples, the ceiling 706 is coupled to the housing 702 through the use of any suitable fasteners, such as pins 1100. Without limitation, suitable fasteners may include nuts and bolts, washers, screws, pins, sockets, rods and studs, hinges and/or any combination thereof. With additional reference to FIG. 7, pins 1100 are disposed through the post holes 1012 in the ceiling 706 and the holes 932 in the housing 702 to attach the ceiling 706 to the housing 702. The ceiling 706 may be positioned on the housing 702 such that the cantilever tabs 1000 are disposed over the inclined surfaces 918 in the housing 702. In addition, the ceiling 706 may also be positioned on the housing 702 such that the arm holes 1016 are disposed over the tabs 717 on the arms 704, enabling engagement of the tabs 717 through the arms holes 1016 for rotation of the arms 704.

Figure 12:
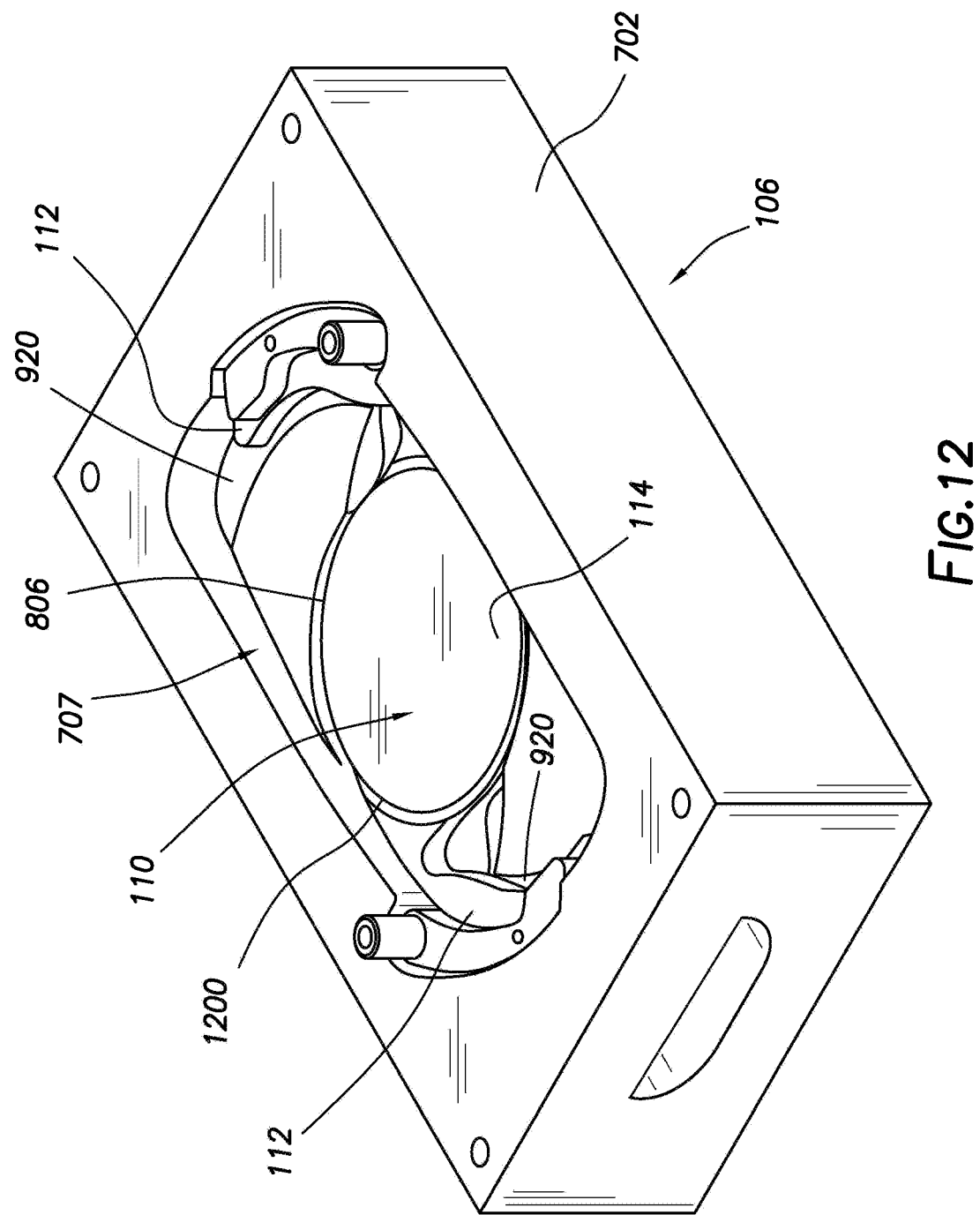
FIG. 12 illustrates an IOL in a housing of the haptic optic management system of FIG. 7.

With reference now to FIGS. 12-16, operation of the HOMS 106 will be described in detail. For illustrative purposes, the ceiling 706 is not shown on FIGS. 12 and 13. As depicted in FIG. 12, the IOL 110 is disposed in the housing 702. In the illustrated example, the IOL 110 is disposed in the cavity 707 in order to pre-load the HOMS 106. The IOL 110 is placed into the cavity 707 in a relaxed or initial state, wherein the haptics 112 extend from the optic 114. The haptics 112 are disposed on the haptic platforms 920. (e.g., shown on FIG. 8). A periphery 1200 of the optic 114 may be at least partially disposed on optic platform 917 (e.g., shown on FIG. 9).

Figure 13:
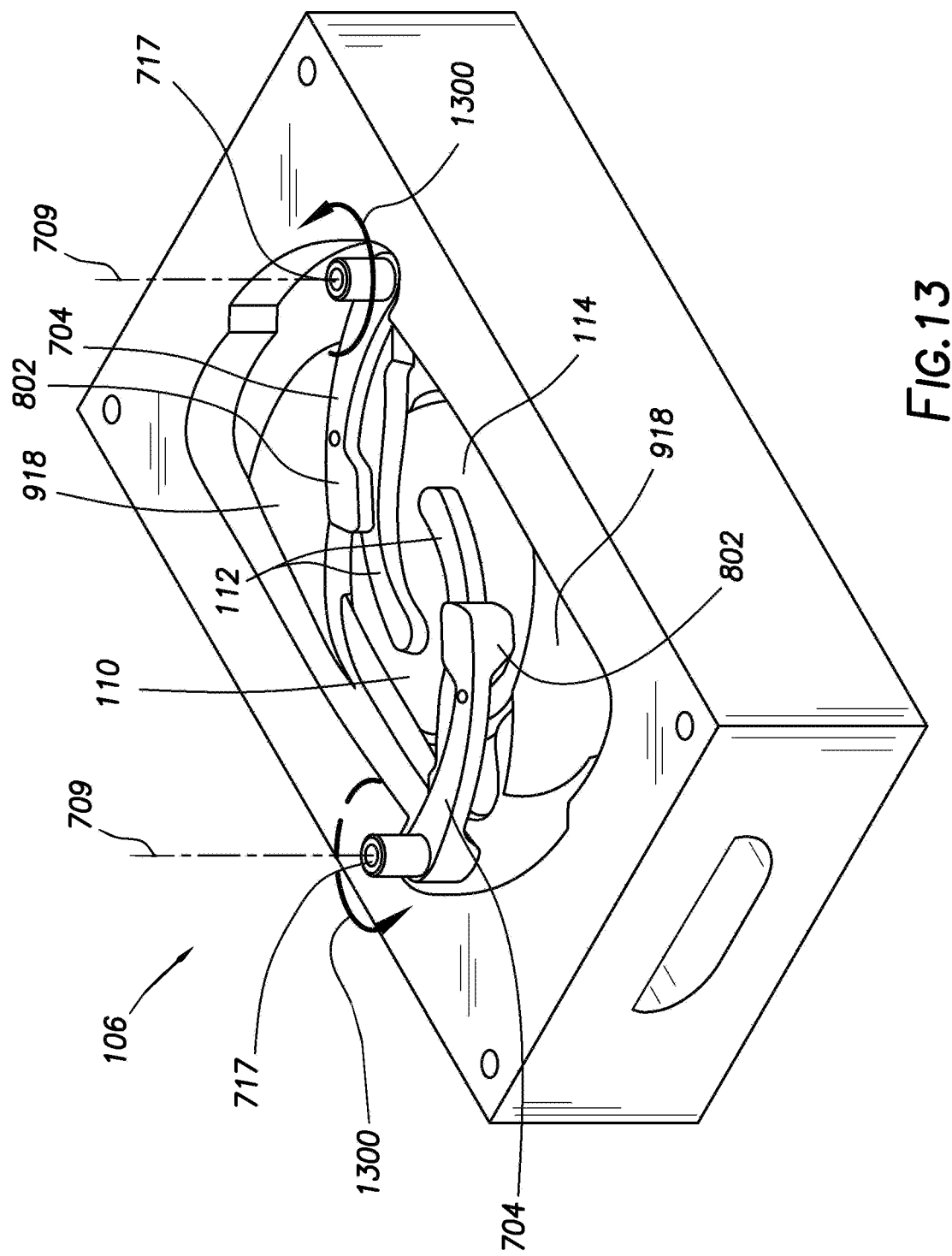
FIG. 13 illustrates the haptic optic management system of FIG. 7 in operation.

With the IOL 110 disposed in the housing 702, the arms 704 may be actuated to move the haptics 112 onto the optic 114 as shown on FIG. 13. As previously described, examples include application of a force onto tabs 717 of the arms 704 to cause the arms 704 to rotate about respective axes 709. As illustrated, the arms 704 each rotate about the axes 709 in the direction shown by an arrow 1300. As the force causes the arms 704 to rotate and move, the arms 704 engage the haptics 112 of the IOL 110 causing them to move up the inclined surfaces 918. In some embodiments, continued rotation of the arms 704 folds the haptics 112 on top of and over the optic 114. In the illustrated example, the second end 802 of the arms 704 engages the haptics 112, thereby moving the haptics 112 along the inclined surfaces 918 of the housing 702. As the haptics 112 move along the inclined surfaces 918, the haptics 112 move upward such that the haptics 112 move off the inclined surfaces 918 and on top of the optic 114 of the IOL 110.

Figure 14:
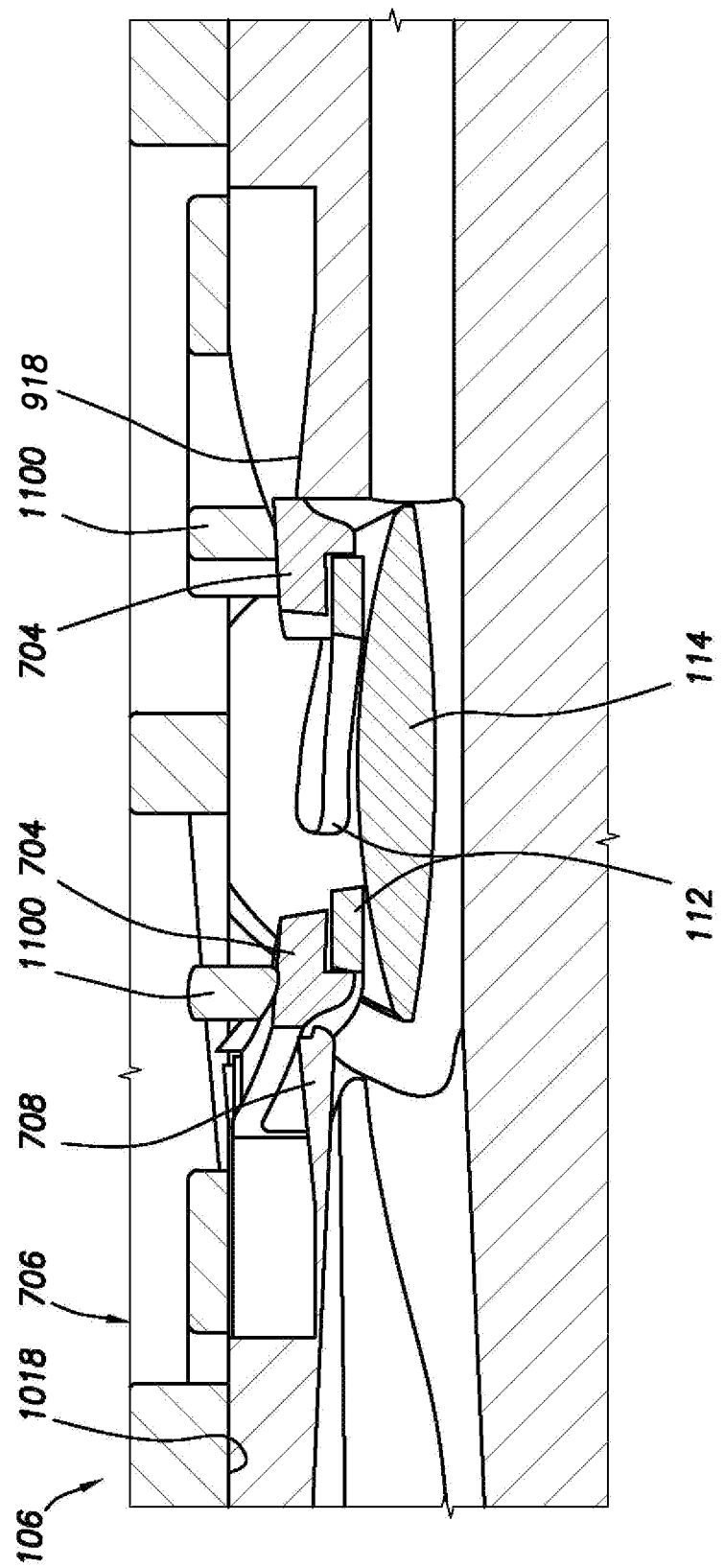
FIG. 14 illustrates a cross-sectional, side-view of the haptic optic management system of FIG. 7.
Figure 15:
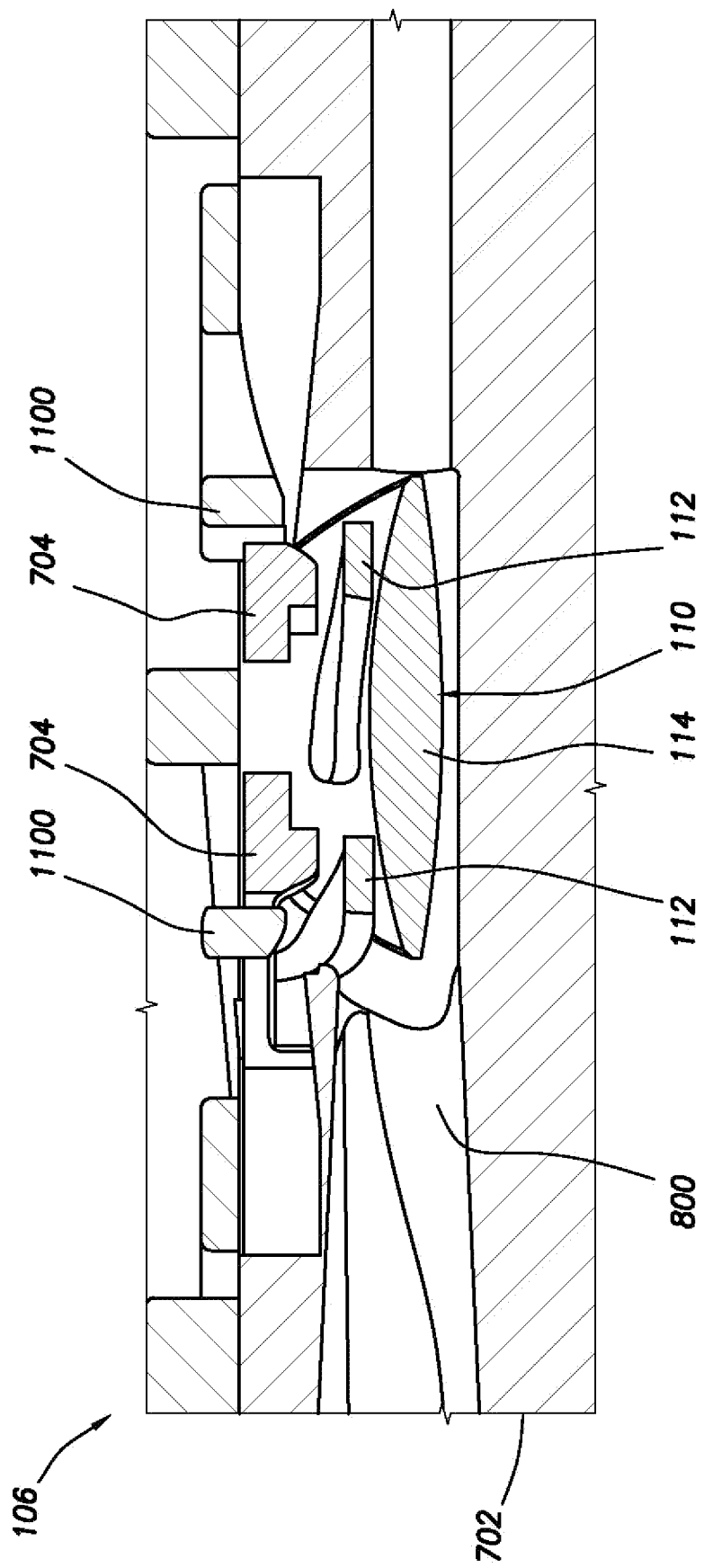
FIG. 15 illustrates a cross-sectional, side-view of the haptic optic management system of FIG. 7 in operation.
Figure 16:
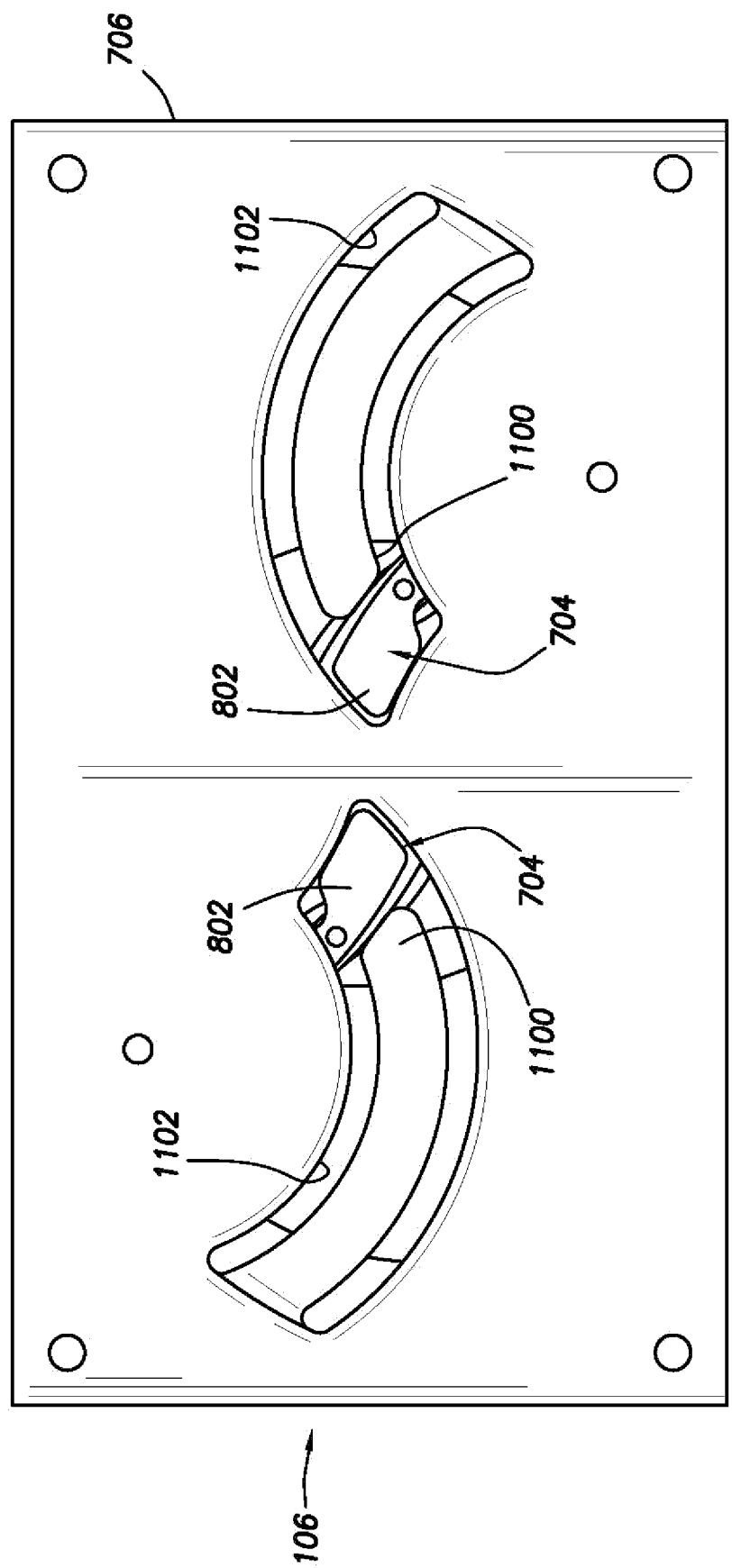
FIG. 16 illustrates a top view of the haptic optic management system of FIG. 7.

Once the arms 704 reach the end of the inclined surfaces 918, the arms 704 deflect downwards by the cantilever tabs 1000 disposed on the ceiling 706, as depicted in FIG. 14. As previously described, the cantilever tabs 1000 protrude from the bottom face 1018 of the ceiling 706. At this point, the haptics 112 are folded over on top of the optic 114. As illustrated in FIG. 15, there is continued rotation of the arms 704 past the cantilever tabs 1000. The arms 704 continue to push against the haptics 112 during this rotation causing the optic 114 to fold in upon itself as the haptics 112 are positioned above the optic 114. Additionally, as the arms 704 move past the cantilever tabs 1000, the pressure applied to the arms 704 by the cantilever tabs 1000 is released and the arms 704 spring upwards past the tabs 1000. FIG. 16 illustrates a top view of the HOMS 106 after the arms 704 have rotated past the tabs 1000. As illustrated in FIG. 16, the second end 802 of each of the arms 704 is positioned past the cantilever tabs 1000 disposed in the slots 1102 in the ceiling 706. Referring again to FIG. 15, once past the tabs 1000, the arms 704 are no longer in engagement with the haptics 112 and the IOL 110 falls into the bore 900 in the housing 702. A drive system, such as drive system 102 shown on FIG. 1, may then be used to dispense the IOL 110 from the housing 702. Accordingly, the haptic optic management system 106 as described herein may be used to prepare the IOL 110 for insertion into the eye 200 (e.g., shown on FIGS. 2A and 2B).

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. A haptic optic management system, comprising:
   a housing configured to receive an intraocular lens, the housing comprising a first end portion, a second end portion, and a central portion, wherein:
   the central portion is configured to accommodate an optic of the intraocular lens,
   the first end portion is configured to accommodate a first haptic of the intraocular lens, and
   the second end portion is configured to accommodate a second haptic of the intraocular lens;

a first arm pivotably coupled to the housing in the first end portion, the first arm configured to engage the first haptic accommodated in the first end portion; and a second arm pivotably coupled to the housing in the second end portion, the second arm configured to engage the second haptic accommodated in the second end portion.

2. The haptic optic management system of claim 1, wherein each of the first arm and the second arm are configured to rotate to fold the first haptic or the second haptic, respectively, over the optic of the intraocular lens.

3. The haptic optic management system of claim 1, wherein the central portion extends a greater distance into the housing than each of the first end portion and the second end portion.

4. The haptic optic management system of claim 1, wherein the central portion further comprises a base and an optic platform, wherein the optic platform laterally is offset from the base and raised relative to the base, and wherein the optic platform is configured to engage a periphery of the optic of the intraocular lens.

5. The haptic optic management system of claim 1, wherein each of the first end portion and the second end portion comprises a haptic platform, and wherein the haptic platform defines one or more surfaces for receiving at least a portion of the first haptic or the second haptic.

6. The haptic optic management system of claim 5, wherein each haptic platform is further configured to support the first arm or the second arm in an unactuated condition.

7. The haptic optic management system of claim 5, further comprising:

an inclined surface disposed between each haptic platform and the central portion, the inclined surface configured to raise the first haptic or the second haptic over the optic of the intraocular lens as the first arm or second arm is actuated.

8. The haptic optic management system of claim 1, further comprising:

a bore formed in the housing and traversing an entire length of the housing, the bore defining a pathway for insertion of a plunger to engage with the intraocular lens and drive the intraocular lens through the housing.

9. An insertion tool for delivery of an intraocular lens into a patient's eye, the insertion tool comprising:

a drive system;
a plunger in communication with the drive system;
a nozzle; and
a haptic optic management system disposed between the drive system and the nozzle for receiving a distal tip of the plunger, wherein the haptic optic management system comprises:

a housing configured to receive an intraocular lens, the housing comprising a first end portion, a second end portion, and a central portion, wherein:
the central portion is configured to accommodate an optic of the intraocular lens,
the first end portion is configured to accommodate a first haptic of the intraocular lens, and
the second end portion is configured to accommodate a second haptic of the intraocular lens;

a first arm pivotably coupled to the housing in the first end portion of the housing, the first arm configured to engage the first haptic accommodated in the first end portion; and a second arm pivotably coupled to the housing in the second end portion of the housing, the second arm configured to engage the second haptic accommodated in the second end portion.

10. The insertion tool of claim 9, wherein each of the first arm and the second arm are configured to rotate to fold the first haptic or the second haptic, respectively, over the optic of the intraocular lens.

11. The insertion tool of claim 9, wherein the central portion extends a greater distance into the housing than each of the first end portion and the second end portion.

12. The insertion tool of claim 9, wherein the central portion further comprises a base and an optic platform, wherein the optic platform laterally is offset from the base and raised relative to the base, and wherein the optic platform is configured to engage a periphery of the optic of the intraocular lens.

13. The insertion tool of claim 9, wherein each of the first end portion and the second end portion comprises a haptic platform, and wherein the haptic platform defines one or more surfaces for receiving at least a portion of the first haptic or the second haptic.

14. The insertion tool of claim 13, wherein each haptic platform is further configured to support the first arm or the second arm in an unactuated condition.

15. The insertion tool of claim 13, further comprising an inclined surface disposed between each haptic platform and the central portion, the inclined surface configured to raise the first haptic or the second haptic over the optic of the intraocular lens as the first arm or second arm is actuated.

16. The insertion tool of claim 9, further comprising:

a bore formed in the housing and traversing an entire length of the housing, the bore defining a pathway for insertion of the plunger to engage with the intraocular lens and drive the intraocular lens through the housing and to the nozzle.

17. A method of delivering an intraocular lens, comprising:

rotating a first arm pivotably coupled to a housing in a first end portion of the housing and a second arm pivotably coupled to the housing in a second end portion of the housing such that each of the first and second arms engages a corresponding haptic that extends from an optic of the intraocular lens to move the corresponding haptic up one or more inclined surfaces and onto the optic;

applying a downward force to the first and second arms as each of the first and second arms continues to rotate while in engagement with the corresponding haptic to cause the intraocular lens to fold in upon itself;

upon the intraocular lens folding upon itself, biasing the first and second arms upwards; and actuating a drive system to dispense the intraocular lens through a nozzle and into an eye, wherein the nozzle is coupled to the housing.

18. The method of claim 17, wherein the intraocular lens is disposed in a central portion of the housing when the intraocular lens is folded upon itself, the central portion of the housing disposed between the one or more inclined surfaces.

19. The method of claim 17, wherein upon the intraocular lens folding upon itself, the intraocular lens is transferred into a bore in the housing as the first and second arms are biased upwards.

20. The method of claim 19, wherein the intraocular lens is dispensed from the nozzle via a plunger coupled to the drive system.

* * * * *